US010561230B2

(12) United States Patent
Sabet et al.

(10) Patent No.: US 10,561,230 B2
(45) Date of Patent: Feb. 18, 2020

(54) FINGER MOUNTED TOOTHBRUSH WITH AN INTERNAL REINFORCING SKELETON

(71) Applicant: Waggletooth, LLC, Chapel Hill, NC (US)

(72) Inventors: Julienne Sabet, Chapel Hill, NC (US); Thomas Perez Eustis, Jr., Arden, NC (US)

( * ) Notice: Subject to any disclaimer, the term of this patent is extended or adjusted under 35 U.S.C. 154(b) by 161 days.

(21) Appl. No.: 15/910,440

(22) Filed: Mar. 2, 2018

(65) Prior Publication Data

US 2018/0250105 A1 Sep. 6, 2018

Related U.S. Application Data

(60) Provisional application No. 62/466,218, filed on Mar. 2, 2017.

(51) Int. Cl.
*A46B 5/04* (2006.01)
*A61C 17/00* (2006.01)
*A41D 13/08* (2006.01)
*A46B 7/04* (2006.01)

(52) U.S. Cl.
CPC ............... *A46B 5/04* (2013.01); *A46B 7/04* (2013.01); *A61C 17/00* (2013.01); *A41D 13/087* (2013.01); *A46B 2200/1066* (2013.01); *A46B 2200/1093* (2013.01)

(58) Field of Classification Search
CPC .. A46B 5/04; A46B 9/005; A46B 9/04; A46B 2200/1086; A41D 13/087; A61C 17/00; A61H 13/00; A61F 13/105; D05B 91/04; A01K 13/001
USPC .......... 15/227; 2/21; 223/101; 601/139, 141; 433/1
See application file for complete search history.

(56) References Cited

U.S. PATENT DOCUMENTS

| | | | | |
|---|---|---|---|---|
| 2,096,858 A | * | 10/1937 | Purcell | A45D 40/28 132/320 |
| 2,511,557 A | * | 6/1950 | Arnold | A45D 40/28 15/227 |
| 8,522,391 B1 | * | 9/2013 | Safieh | A46B 5/04 15/110 |
| 2016/0015161 A1 | * | 1/2016 | Mullen | A46B 5/04 433/216 |

* cited by examiner

*Primary Examiner* — Mark Spisich
(74) *Attorney, Agent, or Firm* — Carla Gannon Law

(57) ABSTRACT

A finger mounted toothbrush system includes a sheath constructed of a flexible, textured substrate; a rigid, pronged skeleton that fits into the substrate; and a retaining ring that secures the sheath to the skeleton. Prongs of skeleton may be constructed of thermoplastic that can be hardened to fit a user's finger size.

15 Claims, 2 Drawing Sheets

FINGER MOUNTED TOOTHBRUSH WITH AN INTERNAL REINFORCING SKELETON

CROSS-REFERENCE TO RELATED APPLICATIONS

This application claims the benefit of U.S. Provisional Patent Application Ser. No. 62/466,218 entitled FINGER MOUNTED TOOTHBRUSH WITH BITE PROTECTION, filed Mar. 2, 2017. The provisional application is incorporated by reference in its entirety into the present application.

BACKGROUND

Field

The present invention relates generally to oral care and, more particularly, to a finger mounted toothbrush having an internal reinforcing skeleton for use with humans and other animals.

Related Art

Brushing the teeth of another person or animal, for example a child or pet, can be a very challenging task. It can also be uncomfortable or even dangerous to the one whose teeth are being brushed (the "recipient") because the person performing the brushing (the "user") is not always aware of the position or pressure of the brush-head because they are receiving tactile information only from the handle they are manipulating. Known finger mounted toothbrushes overcome some of the shortcomings of conventional handled toothbrushes by allowing the user to better control the position, pressure and motion while brushing.

Known finger mounted toothbrushes, however, are less than ideal insofar as the user may be inadvertently or intentionally bitten by the recipient. Moreover, the fear of injury may cause the user to be tentative and cautious, which can affect the frequency, duration or quality of the dental hygiene being performed.

As can be seen, there is a need for a finger mounted toothbrush that provides optimal oral care to the recipient, while protecting the user from injury. It is desirable that this toothbrush is easy to use, effective, and economical to produce and transport.

SUMMARY OF THE INVENTION

The present invention is directed to a finger mounted toothbrush with an internal reinforcing skeleton. The toothbrush system generally includes a sheath constructed of a flexible, textured substrate; a rigid, pronged skeleton that fits into the substrate; and a retaining ring that secures the sheath to the skeleton.

Accordingly, one aspect of the present invention is to provide a toothbrush system that cleans a recipient's teeth in a comfortable and efficient manner. Another aspect of the present invention is to provide a toothbrush system that is easy and safe for a user.

These and other aspects of the present invention will become apparent to those skilled in the art after a reading of the following description of the preferred embodiment when considered with the drawings.

DESCRIPTION OF THE PREFERRED EMBODIMENTS

The following detailed description discusses the best currently contemplated modes of carrying out exemplary embodiments of the invention. The description is not to be taken in a limiting sense, but is made merely for the purpose of illustrating the general principles of the invention.

The following structure numbers apply among the various FIGS.:
10—Toothbrush system;
20—Sheath;
22—Substrate;
24—Opened end;
25—Closed end;
30—Skeleton;
32—Prong;
33—Distal end of prong;
34—Base;
35—External circumference;
37—Gripping protrusions;
38—First threads;
40—Retaining ring;
42—Internal circumference;
43—Second threads;
50—User; and
60—Recipient.

Figure 1:
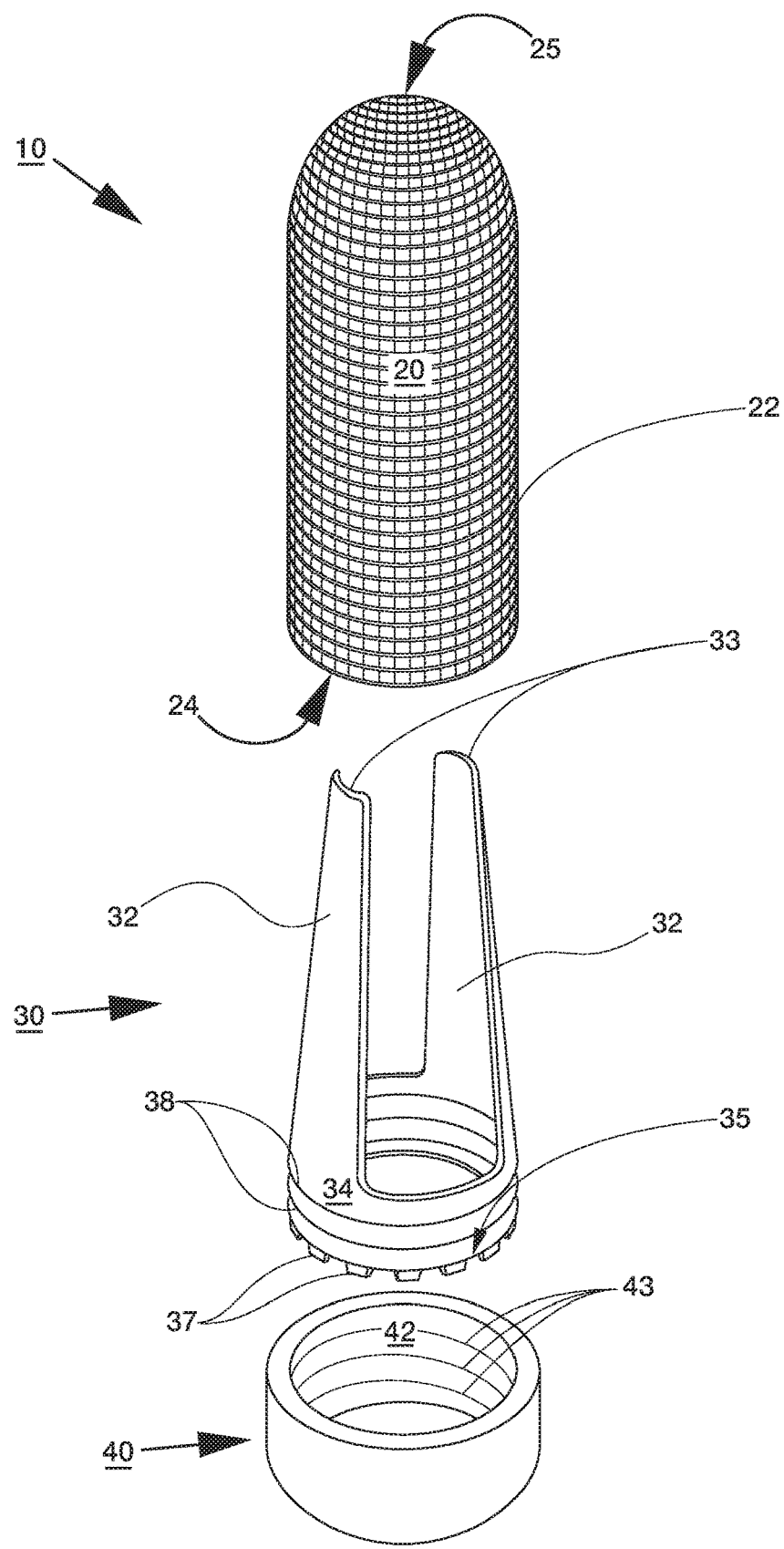
FIG. 1 is an exploded view of an embodiment of the invention with a portion of the substrate enlarged to show texture.
Figure 2:
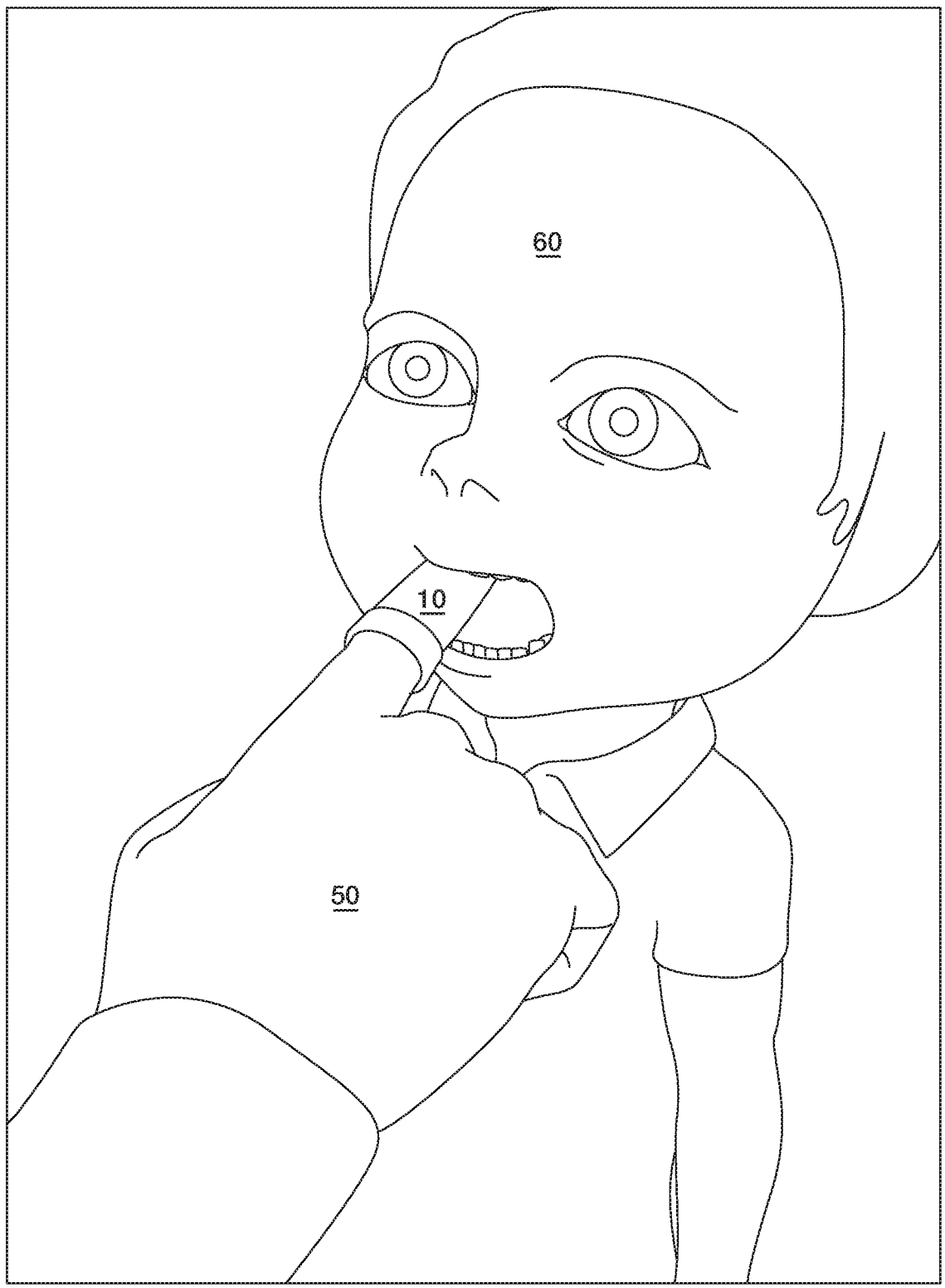
FIG. 2 depicts the invention in use.

Referring now to the drawings in general and FIG. 1 in particular, it will be understood that the illustrations are for the purpose of describing a preferred embodiment of the invention and are not intended to limit the invention thereto. As best seen in FIG. 1, there are three main components to toothbrush system 10: sheath 20; skeleton 30; and retaining ring 40.

Sheath 20 is preferably constructed of flexible substrate 22 such as non-woven polyethylene terephthalate (PET) that is ultrasonic welded to form a quilted texture. In a preferred embodiment, substrate 22 is approximately 0.3-0.5 mm thick, with raised portions approximately 0.5-1 mm high relative to non-raised portions, and spaced approximately 0.75-1 mm apart. The sheath can be formed of other substrates, preferably that are mildly abrasive. The sheath may include bristles, or may be bristleless, and may have a "fuzzy" texture.

Sheath 20 preferably fits over the distal end of an average sized human finger, past the metacarpophalangeal joint. In a preferred embodiment sheath 20 is approximately 58.5-71.5 mm long, but approximately 65 mm long is preferred, and has a circumference of approximately 28.8-35.2 mm, but 32 mm is preferred, at opened end 24. Sheath 20 may be formed from a flat substrate that is joined along the edges to form a tubular structure, then preferably turned inside out so the outer surface of sheath 20 is seamless. Sheath 20 should be slightly longer in length than skeleton 30 so that sheath can be tucked inwardly, between skeleton and retaining ring 40, as described below.

Skeleton 30 is preferably formed of a rigid material such as a polymer, thermoplastic, metal, or composite, and generally includes base 34 having multiple threads first 38 on the external circumference 35, and a plurality of gripping protrusions 37 along bottom circumference of base. At least two prongs 32 extend upwardly from base 34, and terminate in distal end of prongs 33. The prongs each preferably taper inwardly towards distal end of prongs 33. Also, prongs 32 preferably taper inwardly one-to-another, such that distal ends of prongs 33 are closer in distance than prongs proximal to base 34. These prongs reduce the risk of injury to the user by dispersing a bite-forcer over the protected finger region, versus a direct bite. In a preferred embodiment, skeleton 30 is approximately 58.5-71.5 mm tall from distal end of prong 33 to tip of gripping protrusion 37, with approximately 65 mm tall being preferred. Base 34 has a diameter of approximately 28.8-35.2 mm, with 32 mm being preferred. Each prong 32 is approximately 58.5-71.5 mm tall, with approximately 65 mm tall being preferred.

Retaining ring 40 includes second threads 43 defined by internal circumference 42. It is preferably constructed of a rigid material such as a polymer, thermoplastic, metal, or composite. First threads 38 of base 34 engage with second threads 43 of retaining ring 40. Internal circumference 42 of retaining ring preferably has diameter of approximately 28.8-35.2 mm, with 32 mm being preferred.

In use, toothbrush system 10 is assembled by slipping sheath 20 over skeleton 30 so open end of sheath 20 extends slightly beyond gripping protrusions 37. Retaining ring 40 and/or base 34 are rotated to engage first threads 38 with second threads 43, thereby resulting in securing skeleton to retaining ring while cinching bottom edge of sheath 20 between gripping protrusions 37 and retaining ring 40. A user then slips their finger into the toothbrush by inserting into open end of sheath and pushing in until it comes in contact with closed end 25 of sheath. One prong of skeleton is preferably positioned on the top of the user's finger, with the other prong preferably position on the bottom of the user's finger. The user then cleans the inside of the recipient's mouth by rubbing the teeth and/or gums with sheath 20. Sheath 20 can be replaced by loosening retaining ring 40 from base 34, removing used sheath, and putting on a new sheath.

In one embodiment, prongs 32 are thermoplastic that, in the uncured state, move freely such that distal end of prongs 33 can touch each other and retract outwardly. A user heats uncured prongs, preferably in hot water, then squeezes and holds heated prongs around finger so prongs mold to finger and cure upon cooling. This results in a custom fit.

Specifications of certain structures and components of the present invention have been established in the process of developing and perfecting prototypes and working models. These specifications are set forth for purposes of describing an embodiment, and setting forth the best mode, but should not be construed as teaching the only possible embodiment. Rather, modifications may be made without departing from the spirit and scope of the invention as set forth in the following claims. It should be understood that all specifications, unless otherwise stated or contrary to common sense, are +/−10%, and that ranges of values set forth inherently include those values, as well as all increments between.

We claim:

1. A toothbrush system including:
   A. A flexible tubular sheath having a closed end and an opened end;
   B. A rigid skeleton having a base and at least two prongs directed upwardly, said skeleton configured to fit within said sheath; and
   C. A retaining ring engageable with said base, wherein said sheath, skeleton and retaining ring are separable one from another.

2. The toothbrush system of claim 1 wherein said sheath is constructed of a polyethylene terephthalate substrate.

3. The toothbrush system of claim 2 wherein said substrate is a non-woven.

4. The toothbrush system of claim 2 wherein said substrate has a quilted texture.

5. The toothbrush system of claim 1 wherein said base includes a plurality of gripping protrusions extending downwardly, said protrusions for grasping said sheath.

6. The toothbrush system of claim 1 wherein said base includes an external circumference, said external circumference defining a plurality of first threads.

7. The toothbrush system of claim 6 wherein said retaining ring includes an internal circumference, said internal circumference defining a plurality of second threads.

8. The toothbrush of claim 7 wherein said plurality of second threads are engageable with said plurality of first threads.

9. A toothbrush including:
   A. An elongated tubular sheath having a closed distal end and an opened proximal end, said elongated tubular sheath configured to receive a human finger;
   B. A skeleton within said sheath for buttressing said sheath, said skeleton including exactly two prongs and including a plurality of gripping protrusions at a proximal end engaged with said sheath; and
   C. A retaining ring connected to said proximal end.

10. The toothbrush of claim 9 wherein said prongs are each tapered upwardly.

11. The toothbrush of claim 9 wherein said prongs are tapered towards each other upwardly.

12. The toothbrush of claim 9 wherein said retaining ring is disengageable from said skeleton by unscrewing.

13. A method of performing oral hygiene including the steps of:
   A. Positioning a flexible sheath over a rigid skeleton;
   B. Engaging a retaining ring with said rigid skeleton to secure said sheath to said skeleton;
   C. Rubbing surfaces inside a recipient's mouth with said sheath;
   D. Disengaging said retaining ring from said skeleton; and
   E. Removing said sheath from said skeleton.

14. The method of claim 13 wherein said step of engaging said retaining ring with said rigid skeleton includes the step of engaging corresponding threads.

15. The method of claim 13 further including the step of positioning said sheath on gripping protrusions of said skeleton.

* * * * *